United States Patent
Becker et al.

(10) Patent No.: US 10,448,991 B2
(45) Date of Patent: Oct. 22, 2019

(54) SURGICAL INSTRUMENT HAVING POINT CONTACTS IN COUPLING AREA

(71) Applicant: Aesculap AG, Tuttlingen (DE)

(72) Inventors: Alina Becker, Balgheim (DE); Pedro Morales, Tuttlingen (DE)

(73) Assignee: Aesculap AG (DE)

( * ) Notice: Subject to any disclaimer, the term of this patent is extended or adjusted under 35 U.S.C. 154(b) by 207 days.

(21) Appl. No.: 15/632,526

(22) Filed: Jun. 26, 2017

(65) Prior Publication Data

US 2018/0000536 A1 Jan. 4, 2018

(30) Foreign Application Priority Data

Jun. 29, 2016 (DE) .......................... 10 2016 111 892

(51) Int. Cl.
| | |
|---|---|
| *A61B 17/32* | (2006.01) |
| *A61B 17/29* | (2006.01) |
| *A61B 18/14* | (2006.01) |
| *A61B 17/28* | (2006.01) |
| A61B 17/00 | (2006.01) |
| A61B 90/00 | (2016.01) |

(52) U.S. Cl.
CPC ...... *A61B 18/1445* (2013.01); *A61B 17/2816* (2013.01); *A61B 17/29* (2013.01); *A61B 2017/00477* (2013.01); *A61B 2017/2919* (2013.01); *A61B 2017/2933* (2013.01); *A61B 2090/0813* (2016.02)

(58) Field of Classification Search
CPC ......... A61B 17/00; A61B 17/29; A61B 17/28; A61B 17/3211; A61B 17/3213; A61B 2017/00477; A61B 2017/2933; A61B 2017/2919; A61B 17/32; A61B 2017/32113
See application file for complete search history.

(56) References Cited

U.S. PATENT DOCUMENTS

| | | | |
|---|---|---|---|
| 2006/0122615 A1* | 6/2006 | McKinley | .......... A61B 17/1611 606/83 |
| 2011/0106065 A1 | 5/2011 | Tontarra et al. | |
| 2015/0209060 A1* | 7/2015 | Dmuschewsky | .. A61B 17/1608 606/207 |

FOREIGN PATENT DOCUMENTS

| | | |
|---|---|---|
| AU | 2003235012 A1 | 3/2005 |
| DE | 10101425 A1 | 7/2002 |

(Continued)

OTHER PUBLICATIONS

German Search Report with English language translation for Application No. 10 2016 111 892.3, dated Apr. 28, 2017, 17 pages.

*Primary Examiner* — Vi X Nguyen
(74) *Attorney, Agent, or Firm* — RatnerPrestia

(57) ABSTRACT

A surgical instrument includes a female branch defining in a coupling area a hollow volume including inwardly facing inner coupling surfaces and including a male branch which can be pivoted relative to the female branch at least partly inside the hollow volume about a pivot axis, the male branch defining in the coupling area a guide portion having outwardly facing outer coupling surfaces in which outer coupling recesses are arranged, wherein on the inner coupling surfaces, inner coupling recesses are arranged which extend relative to a longitudinal axis of the surgical instrument in a direction other than that of the outer coupling recesses.

9 Claims, 3 Drawing Sheets

(56) References Cited

FOREIGN PATENT DOCUMENTS

| DE | 202009014310 U1 | 3/2010 |
|----|-----------------|--------|
| DE | 202011000800 U1 | 5/2011 |
| DE | 102012209247 A1 | 12/2013 |

* cited by examiner

SURGICAL INSTRUMENT HAVING POINT CONTACTS IN COUPLING AREA

RELATED APPLICATION(S)

This application is related to and claims the benefit of priority of German Application No. DE 10 2016 111 892.3, filed Jun. 29, 2016, the content of which is incorporated by reference herein in its entirety.

FIELD

The present invention relates to a surgical instrument comprising at least two instrument parts which can be pivoted relative to each other or else comprising at least one stationary instrument part and one movable (e.g. branch spring on bar) instrument part. Surgical/medical instruments of the type according to the invention, for example, may primarily be clamps, gripping devices, cutting device and/or retaining devices of any geometry used in surgery.

BACKGROUND

Surgical instruments which ensure a relative movement between branches/instrument parts, are applied in almost all medical fields. Efficient just as thorough purification/disinfection/sterilization of used instruments becomes increasingly important. The reason for this is, on the one hand, to meet an increasing quality standard with respect to disinfection, on the other hand, the time interval available for disinfection is more and more reduced. Pivoting of two or more branches/instrument parts (forming the jaw member of the instrument) usually is enabled in a coupling area. The latter is configured so as to realize robust and uniform guiding of the branches relative to each other. Due to the mutual support of the branches/instrument parts such guiding usually involves surfaces which are hardly accessible to a disinfectant, thereby, on the one hand, thorough disinfection being impeded and, on the other hand, a lot of time being required for disinfection.

Several state-of-the-art documents are based on the object of better accessibility of surfaces to be disinfected of a coupling area and/or mounting area. For example, DE 10101425 A1 discloses a surgical instrument comprising two branches capable of being pivoted relative to each other. They are accessible for purification and sterilization of contact surfaces to a restricted extent only. For improving said accessibility in that patent application publication the branches are structurally modified so that outside their normal operating area which relates to usual angular spans of pivoting they are movable relative to each other so that full-surface contacts are reversed in portions. In this way, improved purification is made possible. The original problem, i.e. that in the coupling area of the branches only contact surfaces which are very difficult to disinfect are provided, is not completely eliminated, however.

A generic document is also constituted by DE 20 2009 104 310 U1. It discloses a sliding shaft instrument comprising a main part and a further part which is configured so that an as complete disinfection as possible can be carried out between the two parts without dismounting the two parts. In that document it is not possible, either, to completely avoid full-surface or at least line contacts. Furthermore, it has to be noted that that document includes a pivoting axis which is directed orthogonally to one according to the invention and is located outside a coupling area, which causes the complexity of disinfection to be reduced.

In this respect, for example the disinfection of a through end/box end extremely complex in prior art is mentioned, as it is also known from DE 202011000800 U1. Such disinfection may be carried out by means of fluid or by means of rays and can be performed manually as well as by machine.

SUMMARY

In view of this state of the art, a device is provided for minimizing the points/areas of contact between at least two branches/instrument parts in a coupling area and/or mounting area so that almost all surfaces of the coupling area and/or coupling areas can be reached almost unhindered by a disinfecting medium and at the same time the guiding characteristics of the branches are not impaired.

Accordingly, a surgical instrument includes at least two instrument parts which are hinged to each other in scissors manner or relatively pivotally (each consisting of a branch/ an instrument part and an integrally connected actuating arm including an actuating grip) which in the hinge area have a respective contact surface to the respective other instrument part. The contact surfaces of the at least two instrument parts have surface structures different from each other so that the contact of the two instrument parts with each other is line-shaped and/or point-shaped, especially is made by plural contact points and/or contact lines spread over the predetermined contact surface.

The total contact surface is thus minimized while a stable sliding guide (free from tilting) is maintained, wherein between the contact points and/or contact lines gaps/clearances are formed which can be easily reached by a disinfectant.

From said configuration of the surfaces of the coupling area and/or mounting area the following advantages can thus be derived, for example:

Non-dismountable instruments merely have several point contacts in the coupling area and/or mounting area when two instrument parts are guided relative to each other in a planar manner, thus enabling almost complete disinfection of the coupling surfaces.

The instrument achieves almost complete disinfection while the functionality in all angular spans of the branches relative to each other is unrestricted.

In addition, the disinfectability of the pivoting mechanism is considerably increased by modification of the respective openings/through-openings for a pivot pin.

Improved lubrication of the components movable relative to each other is enabled. Herefrom reduced frictional resistance and improved material preservation are resulting, thus allow the operating comfort and the service life to be increased.

Error reduction when preparing a surgical instrument.

Accordingly, a surgical instrument includes a female branch (instrument part) and, resp., a box branch defining a hollow volume having inwardly facing inner coupling surfaces in a coupling area and/or mounting area. The inner surfaces which are located to be plane-parallel to a frontal plane (reference plane) that will be described in detail in the course of this application are referred to as inner coupling surfaces. The coupling area and/or mounting area may be configured as an inserting end or box end or as a placed-on end and is not formed before the two branches are in an assembled state. The surgical instrument further comprises a male branch (instrument part) or, resp., inserting branch which can be pivoted relative to the female branch at least partly inside the hollow volume about a pivot axis preferably extending normal to the inner coupling surface and which in the coupling area defines a (sliding) guide portion having outwardly facing outer coupling faces in which outer coupling recesses are arranged. The latter are prepared to pass at least partially through the hollow volume. In this way, an inserting end or placed-on end is formed between the two branches and admits a relative pivoting with planar guiding.

Furthermore, inner coupling recesses extending relative to a longitudinal axis of the surgical instrument preferably in a direction other than the outer coupling recesses are arranged on the inner coupling surfaces. Preferably, the shape of the inner coupling recesses substantially corresponds to the shape of the outer coupling recesses. The term "shape" here paraphrases the geometry of a recess in a longitudinal section. The term "direction" comprises the alignment/orientation of a recess in a frontal plane relative to a longitudinal axis. The direction along the longitudinal axis thus corresponds to an angle of 0°, the direction along a transverse axis corresponds to an angle of 90°.

It is further advantageous when the inner coupling recesses are arranged/extend relative to the outer coupling recesses such that the female branch and the male branch are prepared for contacting each other in the coupling area at point contacts. Point contacts constitute the smallest possible bearing face; therefore, they enable almost complete disinfection of the coupling area and thus increase the disinfectability of the entire instrument.

As soon as the inner coupling recesses and/or the outer coupling recesses extend in trough shape over the entire width of the respective branch, the point contacts according to the invention can be efficiently realized. Over the width of a branch at least one recess is preferably continuously formed. It is noted in this context that the recesses are not required to extend in a transverse direction which is orthogonal to the longitudinal axis, but that they extend in any directions, preferably in a direction between the transverse direction and the longitudinal direction.

Another advantageous embodiment consists in the fact that the inner coupling recesses and the outer coupling recesses extend linearly as to their length. The alignment of the recesses thus is not curved (not wave-shaped). Preferably, the width of the respective branches in the coupling area is at least approximately constant over their height. In the longitudinal direction, the width of the branches in the coupling area may decrease in the distal direction. When, moreover, the inner coupling recesses extend in a direction other than that of the outer coupling recesses, it is resulting therefrom that the respective recesses are prevented in each operating state (relative pivoting angle of the instrument parts) from slipping into each other. On the one hand, this increases the operating safety, on the other hand, according to the underlying object of the invention, increased reachability by the disinfectant is thus ensured.

It is of further advantage when a profile of the inner coupling recesses and/or a profile of the outer coupling recesses substantially forms a wave shape in a longitudinal section along a longitudinal axis of the instrument. This brings about a simple geometry of the recesses which can be manufactured in an efficient manner. Preferably, the recesses are milled, ground, cut, etched or indented/embossed into the respective branches.

When the hollow volume has an upper inner coupling surface and a lower inner coupling surface each being provided with inner coupling recesses, and the male branch has an upper outer coupling surface and a lower outer coupling surface each being provided with outer coupling recesses, the support surface of the branches relative to each other is further minimized in the coupling area and the point contacts according to the invention can be shaped in a geometrically defined manner.

Moreover, the target according to the invention is complied with when the inner coupling recesses and the outer coupling recesses extend relative to each other such that the female branch/instrument part and the male branch/instrument part are prepared to contact each other in the assembled state at point contacts in each reachable angular span in a plane which extends to be plane-parallel to a frontal/reference plane described in more detail hereinafter in the coupling area. Point contacts constitute the smallest possible bearing surface between two components, thus allowing disinfection of highest quality to be achieved.

As soon as the inner coupling recesses and/or the outer coupling recesses are formed as a plurality of bulging recesses and the female branch and the male branch are prepared to contact each other in the assembled state in the coupling area, also this embodiment permits a point contact between the two branches. The bulged recesses may also be referred to as recesses in the "golf ball" design. Just as other embodiments of the recesses, they can be manufactured by cutting and by means of both reforming and primary shaping processes.

In addition, it is advantageous when the direction of the inner coupling recesses is inclined with respect to a longitudinal axis of the surgical instrument in a direction of rotation of/about the pivot axis at an angle of from 0° to 90°, preferably at an angle of from 25° to 65°, for example 45°, and the direction of the outer coupling recesses is inclined with respect to the longitudinal axis in the other direction of rotation of/about the pivot axis at an angle of from 0° to 90°, preferably at an angle of 25° to 65°, for example 45°. Hence both recesses extend relative to each other such that a minimum bearing surface is guaranteed and, at the same time, the wave-shaped recesses are prevented from protruding into each other.

Another advantageous embodiment excels by the fact that the female branch and the male branch along the pivot axis include such opening/openings that in said opening a pivot pin can be arranged which causes a positive operative coupling between the female branch and the male branch. Thus, the swivel movement is supported in a sufficiently robust manner, even upon the effect of external shear forces, so that the two branches are exactly and constantly guided toward each other.

The pivot pin may be a rivet, a screw or a comparable fastener.

When the male branch forms a chamfer in an area around the opening, the area around the pivot axis is better accessible to a disinfecting medium, as the inflow of the medium is facilitated. In this way, increased disinfectability of the pivoting mechanism is enabled. The chamfer is preferably milled in and formed as a trough.

In addition, it is advantageous when the opening of the male branch has a substantially rectangular cross-section so that between the opening of the male branch and the pivot pin a line contact can be/is formed. Apart from the rectangular shape, also any polygonal shape such as a triangle or a hexagon is imaginable. For this purpose, the chamfer can be designed in any geometrical shape. In this way, the contact between the individual components of the surgical instrument is further minimized, thereby also the surfaces of the instrument in the area of the openings being increasingly reachable by the disinfecting medium, which entails further enhanced disinfection quality.

It is another advantageous embodiment of the surgical instrument according to the invention that the position of the outer coupling surfaces which is most distant from a frontal plane of the instrument (extending plane-parallel to the upper and lower outer side of the hollow volume) is closer to the frontal plane than or as close to the frontal plane as the position of the inner coupling surfaces which is closest to the frontal plane. In this way, it is ensured in each operating state that no full-surface contact can be made between the inner coupling surface and the outer coupling surface, thus keeping the contact between both components at a minimum. As already discussed, this is strived for according to the invention against the background of optimized disinfectability.

It is equally of advantage when all inner coupling recesses extend in parallel to each other and/or all outer coupling recesses extend in parallel to each other. On the one hand, this permits economic fabrication of the recesses, on the other hand, an appropriate angle between the inner coupling recesses and the outer coupling recesses can thus be chosen so as to make a point contact, and it is not necessary to individually design each point contact.

In a more general embodiment, recesses are introduced in one of the two branches only. By way of example, only the inner coupling surfaces of the hollow volume include recesses, thus bringing about a line contact between the branches in the coupling area. The line contact is superior to a full-surface contact as regards its disinfectability. Alternatively, also only the outer coupling surfaces of the guide portion may have recesses, thus again bringing about a line contact. However, preferably in the outer coupling/contact surfaces, a number of outer coupling recesses is arranged, and on the inner coupling surfaces, a number of inner coupling recesses is arranged which extend relative to a longitudinal axis of the surgical instrument in a direction or directions other than that of the outer coupling recesses.

Apart from a trough-shaped linear configuration and a bulged configuration, the recesses may also take a pyramidal shape, for example. They may be designed as recesses or else as elevations. As afore-mentioned, the geometry of the recesses entailing a point contact is not restricted to these embodiments, however. Rather, the inventive idea functionally comprises all embodiments that bring about a point contact in the coupling area.

The terms "top" and "bottom" within the scope of this application are understood with reference to the following drawings in which they are provided with reference numerals. As a matter of course, when rotating the instrument, an upper surface may point downwards or vice versa. Accordingly, they merely serve for delimiting the surfaces against each other and have no geometric validity in an absolute reference system.

BRIEF DESCRIPTION OF THE DRAWING FIGURES

Hereinafter, the invention shall be illustrated by way of a preferred embodiment with reference to the accompanying Figures, wherein.

The Figures are merely schematic and exclusively serve for the comprehension of the embodiment. Like elements are provided with like reference numerals and can be exchanged for each other.

DETAILED DESCRIPTION

Figure 1:
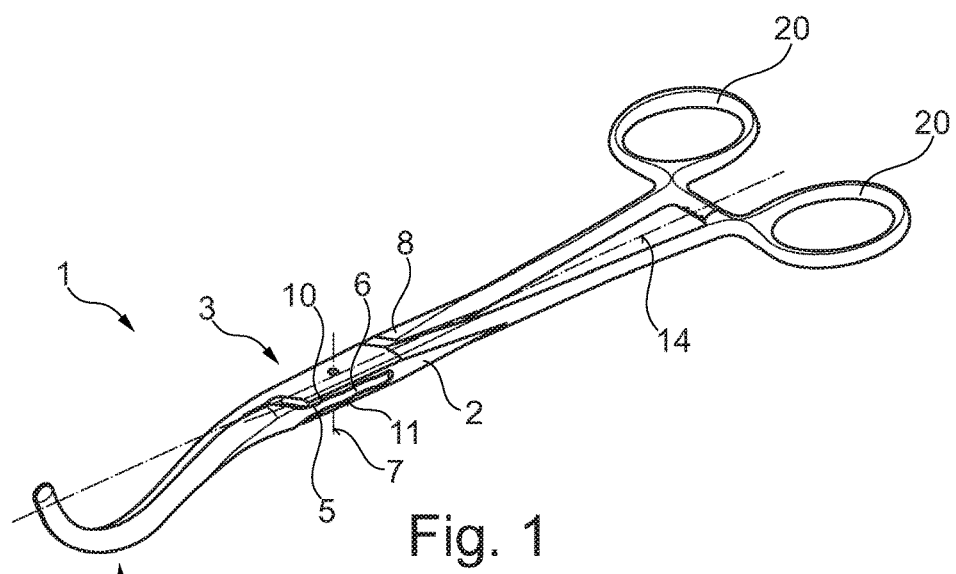
FIG. 1 shows a perspective view of a surgical instrument comprising a female instrument part and a male instrument part in the assembled state.

FIG. 1 shows a perspective view of a surgical instrument 1 according to one embodiment, for example of the clamp and/or scissors and/or forceps design. For this purpose, a female instrument part 2 is operatively coupled to a male instrument part 8 (in a scissors-type manner) so that they can be pivoted relative to each other about a pivot axis 7. Via a proximal grip portion 20 at each instrument part 2, 8 they can be manually pivoted relative to each other so that a distal jaw portion 21 of the surgical instrument 1 is actuated, preferably that two branches defining the jaw portion 21 are moved/swiveled in a clamp/scissors/forceps-type manner so as to increase and/or reduce an engaging gap forming therebetween. The jaw portion 21 may fulfill a clamping, cutting, holding function or any other surgical function. The present jaw portion 21 preferably is a clamp.

Figure 2:
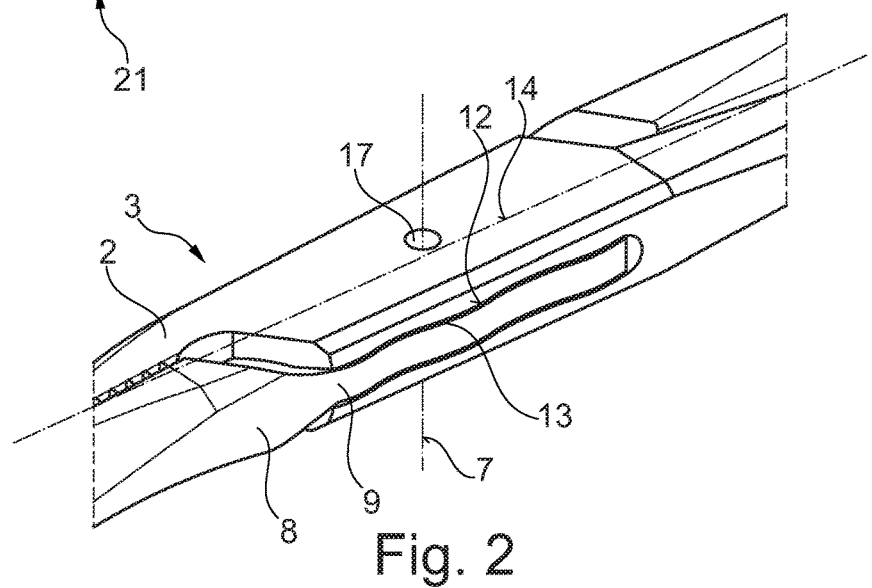
FIG. 2 shows an enlarged perspective view of a coupling area according to the invention.

In a coupling area 3 of the two instrument parts (arms) 2, 8 an inserting end is realized. The functioning thereof shall be explained by way of an enlarged representation in FIG. 2.

Figure 6A:
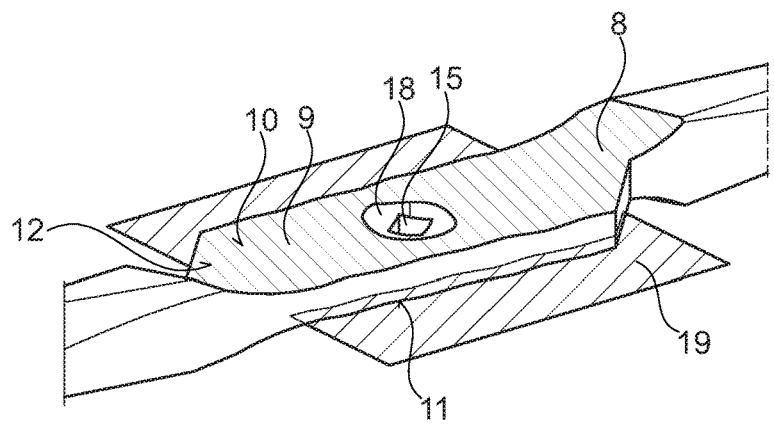
FIG. 6a shows a view of the male instrument part.
Figure 7A:
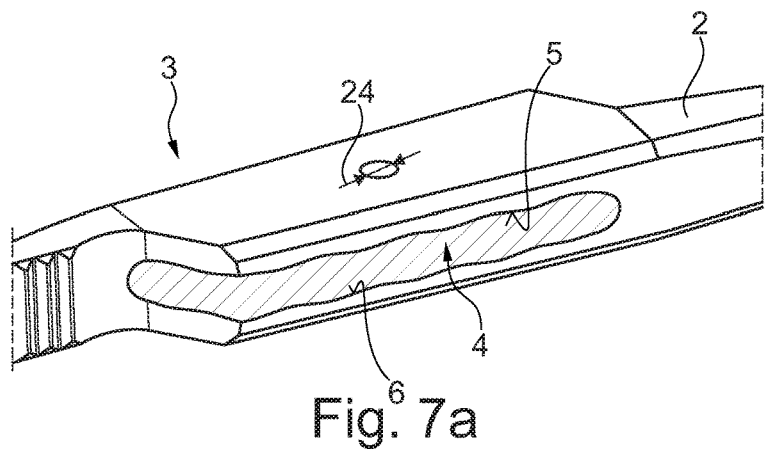
FIG. 7a shows a view of the female instrument part.
Figure 7B:
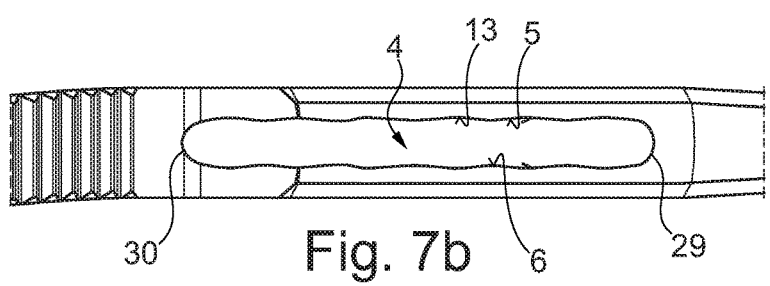
FIG. 7b shows another view of the female instrument part.

A (sliding) guide portion 9 of the male instrument part 8 passes through a hollow volume (slotted hole) 4 formed by the female instrument part 2 which is shown in an enlarged form in FIGS. 7a and 7b. A contact is established between an upper outer coupling surface 10 of the male instrument part 8 and an upper inner coupling surface 5 of the hollow volume 4 (and, resp., of the female instrument part 2). Equally, a lower outer coupling surface 11 of the male instrument part 8 and a lower inner coupling surface 6 of the hollow volume 4 (and, resp., of the female instrument part 2) contact each other. In accordance with the invention, recesses (and/or projections) are arranged/formed in the respective coupling surfaces 5, 6, 10, 11. The hollow volume 4 has a number of inner coupling recesses 13 at the upper and/or lower inner coupling surfaces and the guide portion 9 has a number of outer coupling recesses 12 at the upper and/or lower outer coupling surfaces. The recesses 13, 12 (and the projections resulting therefrom) are aligned so that the instrument parts 2, 8 are (slidingly) guided to be pivoting relative to each other. By the term "aligned" in this context the direction is meant in which the recesses 13, 12 extend in a frontal plane 19 inserted in FIG. 6a which basically symbolizes the contact plane(s) of the two instrument parts.

Figure 4:
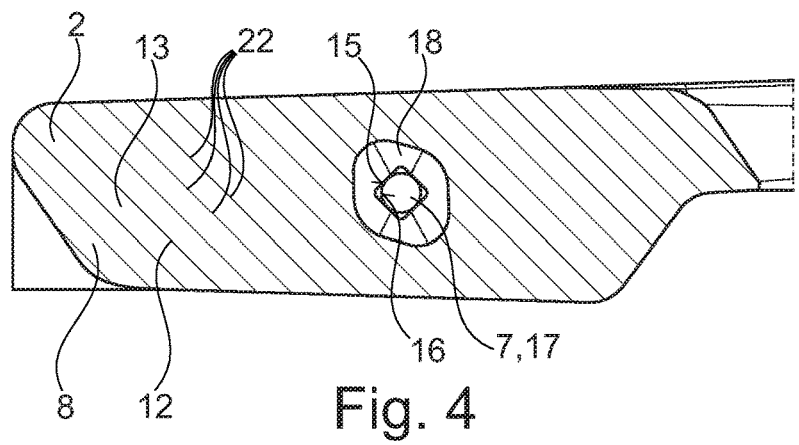
FIG. 4 shows a top view onto the coupling area in which the alignment of the recesses is shown.

According to the invention, the way/type of contact of the two instrument parts is characterized by a number of point and/or line contacts 22 evident in FIG. 4 such that the male instrument part 8 is (slidingly) guided in the hollow volume 4 so that, despite robust and precise guiding (free from tilting), the surgical instrument 1 realizes little opening/ actuating resistance.

As indicated already, the alignment/orientation of the inner coupling recesses 13 is different from that of the outer coupling recesses 12. In this way, preferably point supports/ point contacts 22 between the female instrument part 2 and the male instrument part 8 are made possible. Point contacts (spread over a defined surface) are the smallest possible support of the two instrument parts which allows for optimum disinfectability even between the instrument parts. By the fact that a plurality of point contacts 22 is brought about by the differently orientated inner coupling recesses 13 (and, resp., the thus formed projections) and outer coupling recesses 12 (and, resp., the thus formed projections) the surgical instrument is further (swivel)-guided so that sensitive surgical actions can be comfortably taken by means of the instrument 1 according to the invention.

For interconnecting the two instrument parts 2, 8 a pivot pin 17 is additionally arranged. Said pin can be rotated about the pivot axis 7 which extends orthogonally to a longitudinal axis 14 of the instrument 1. The pivot pin 7 is preferably designed as a rivet.

Figure 3:
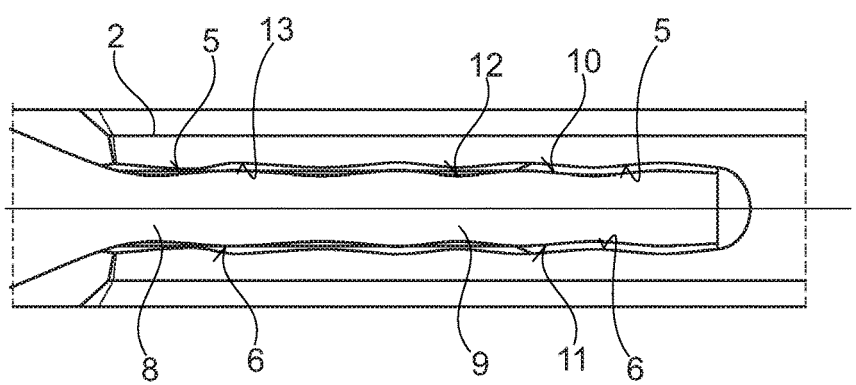
FIG. 3 shows a side view of the coupling area having wave-shaped recesses.

FIG. 3 represents the coupling area 3 of both instrument parts 2, 8 in a lateral view. A configuration of the inner and, resp., outer coupling recesses 13, 12 according to the invention is evident here. The recesses 13, 12 are wave-shaped in the lateral view. The amplitude of the wave shape is small as compared to the wave length. Thus, the point contact according to the invention between the contacting surfaces of the two instrument parts can be realized without a lot of material having to be abraded, for example by means of a milling step, which minimizes the manufacturing expenditure for the recesses 13, 12. The different alignment of the recesses 13, 12 causes the two instrument parts 2, 8 to preferably contact each other always at points, even if the inner coupling recesses 13 have a shape and/or a profile identical to the outer coupling recesses 12.

It is mentioned that the configuration of the recesses 13, 12 is not limited to the afore-described shape. It is equally possible to carry out stepped or other recesses. In addition, the inner coupling recesses 13 may have a shape other than that of the outer coupling recesses 12. The concrete geometric configuration is merely subjected to the requirement of materializing very high disinfectability by retaining clearances adapted to be penetrated by disinfectant between the contact points.

The different alignment/direction/orientation of the recesses 13, 12 is illustrated in FIG. 4. The lines inserted here reproduce the directions of the recesses 13, 12. While the inner coupling recesses 13 are inclined in the one direction with respect to the longitudinal axis 14 of the instrument 1, the outer coupling recesses 12 are inclined to the corresponding other (opposite) direction so as to obtain the point contacts (points of contact) provided with reference numeral 22 in FIG. 4. The inner coupling recesses 13 mutually have the same orientation in the present embodiment. This applies mutatis mutandis also to the outer coupling recesses 12.

Along the longitudinal direction 14 of the instrument 1 in a central area of the coupling area 3, in an advantageous embodiment of the surgical instrument 1, a chamfer 18 is arranged/formed in the area of an opening/through-opening 15 of the male instrument part 8. The chamfer 18 is formed in an area of the male instrument part 8 around the pivot axis 7 and, resp., the pivot pin 17 in the form of a trough. It fulfills the function that the pivot pin 17 and its contact surface and, resp., contact line with the female instrument part 2 and the male instrument part 8 can be better reached by a disinfecting medium. The depth of the chamfer 18 is variable, as long as it ensures that the area around the pivot pin 17 is easily accessible to the disinfecting medium.

Furthermore, in FIG. 4 the contour of the opening/through-opening, approximately in the type of a through-opening, 15 of the male instrument part 8 and the contour of an opening/through-opening 16 of the female instrument part 2 are evident. Whereas the opening/through-opening 16 of the female instrument part 2 substantially takes the shape of the cross-section of the pivot pin 17, i.e. in the present case a substantially circular shape, the opening/through-opening 15 of the male instrument part 8 is substantially rectangular. This substantially rectangular shape of the opening/through-opening 15 causes a line contact to be brought about between the pivot pin 17 and the male instrument part 8 instead of a full-surface contact. Thus, the disinfectability of the surgical instrument 1 is further improved in this way. The substantially rectangular shape of the opening/through-opening 15 is preferably realized by means of rounded corners. Apart from a rectangular shape, for the opening/through-opening 15 the shape of any polygon is appropriate for materializing the line contact.

Figure 5A:
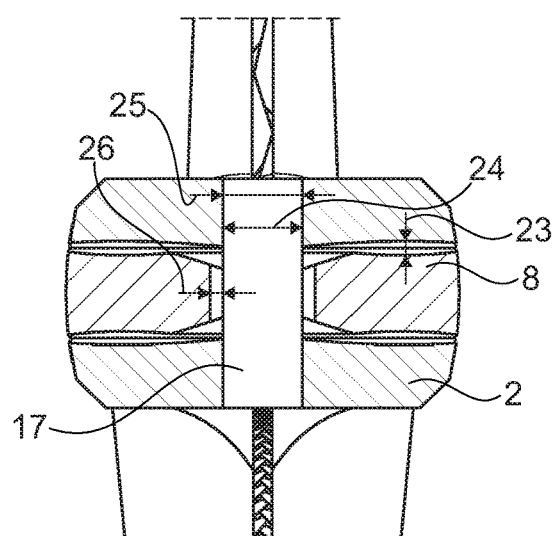
FIG. 5a shows a perspective sectional view across the coupling area level with a pivot axis.

FIG. 5a illustrates a section across the coupling area 3 in a transversal plane level with the pivot pin 17. The length of the pivot pin 17 substantially corresponds to the height of the female instrument part 2 in the coupling area 3. A transverse gap 23 caused by the recesses 13, 12 when a contact is made between the two instrument parts exhibits a varying height in the transversal plane due to the different alignment of the recesses 13, 12. This causes good reachability for the disinfecting medium. Said reachability is further increased by the chamfer 18 as well as the substantially rectangular opening/through-opening 15. An outer diameter 24 of the pivot pin 17 substantially corresponds to an inner diameter 25 of the opening/through-opening 16. On the other hand, a width of the opening 15 is larger than the outer diameter 24, thus causing clearances 26 to be retained between the pin 17 and the opening/through-opening 15 (in the corners of the rectangular shape thereof). Their effect of increased disinfectability of the surgical instrument 1 according to the invention, especially in the area between the pivot pin 17 and the through-opening 15, has been discussed in the foregoing already.

Figure 5B:
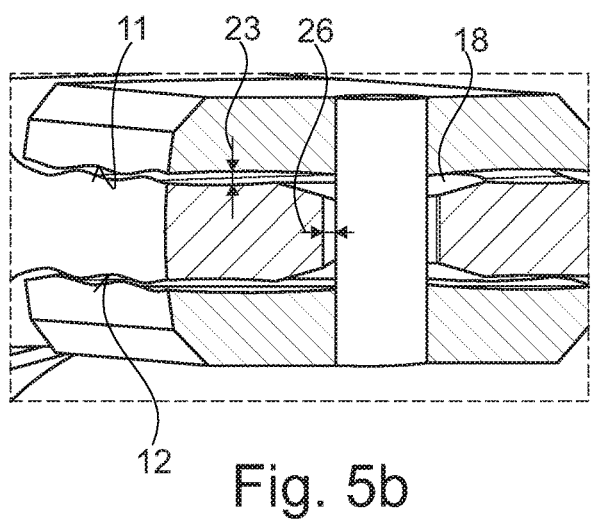
FIG. 5b shows another perspective sectional view across the coupling area level with a pivot axis.

FIG. 5b shows the section in the transversal plane of FIG. 5a in a perspective view. Here the transverse gap 23 is visible more clearly. The latter is configured by means of recesses 13, 12 so as to enable guiding of the two branches 2, 8 relative to each other which is substantially free from play and robust, while disinfectability is optimized according to the invention.

FIG. 6a represents the guide portion 9 of the male instrument part 8 per se. Accordingly, the crest/crests of the outer coupling recesses 12 is/are visible. The chamfer 18 is known, just as the substantially rectangular opening/through-opening 15, from the preceding Figures. An aforementioned frontal plane 19 forms a central plane of the male instrument part 8 as well as of the entire surgical instrument 1. The frontal plane 19 is formed between the upper outer coupling surface 10 and the lower outer coupling surface 11 defining the height of the male instrument part 8 in the coupling area 3. Said height is variable along the longitudinal axis 14 of the instrument 1 by reason of the outer coupling recesses 12.

Figure 6B:
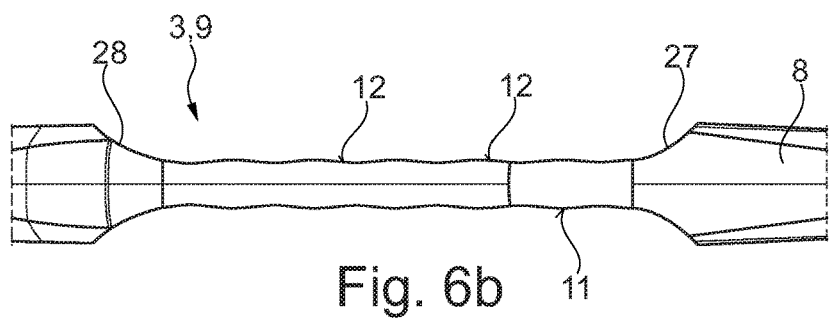
FIG. 6b shows another view of the male instrument part.

FIG. 6b illustrates the guide portion 9 of the male instrument part 8 of FIG. 6a in a lateral view. The wave-shaped configuration of the outer coupling recesses 12 is designed uniformly over each individual outer coupling recess 12. As is evident, the guide portion including its two (upper and lower) sliding guide surfaces is formed by milling off/into the instrument part, wherein both an inlet area 27 of the male instrument part 8 into the guide portion 9 and an outlet area 28 spaced herefrom in the longitudinal instrument direction are configured to be rounded (rounded fillets). Hence a smooth transition is facilitated for the flow of force inside the instrument part 8 and no sharp edges/corners in which dirt may get caught are formed. The guide portion 9 has a smaller height than the instrument part 8 in the inlet and outlet areas 27, 28. In this way, the hollow volume 4 of the female instrument part 2 can be passed/pushed through without the male instrument part being allowed to slip out of the hollow volume again after mounting thereof. The shape of the male instrument part 8 and the shape of the guide portion 9 are not reduced to the ones shown in FIGS. 6*a* and 6*b*. Rather, the inventive idea comprises all geometries enabling a point contact face between the individual branches 2, 8.

FIGS. 7*a* and 7*b* show the female instrument part 2 per se. FIG. 7*a* illustrates the crests of the inner recesses 13. The hollow volume 4 is formed between the upper inner coupling surface 5 and the lower inner coupling surface 6. Analogously to the height of the guide portion 9, also the height of the hollow volume 4 is varied along the longitudinal axis 14 of the instrument due to the inner coupling recesses 13. The inner diameter 25 is prepared for receiving the pivot pin 17.

FIG. 7*b* illustrates the hollow volume 4 of the female instrument part 2 in the lateral view. The female instrument part 2 thus forms an inlet area 29 into the hollow volume 4 which is configured to be rounded so as to facilitate smooth guiding. Moreover, due to the rounding no sharp edges where dirt may get caught are provided. This applies mutatis mutandis to an outlet area 30 of the hollow volume 4. The shape of the female instrument part 2 is not reduced to the shape as shown in FIGS. 7*a* and 7*b*. Rather, the inventive idea comprises all geometries which enable a multiple point contact between the individual instrument parts 2, 8 in the bearing/contact area.

The invention claimed is:

1. A surgical instrument comprising:
    a female instrument part defining in a coupling/hinge area a hollow volume having inwardly facing inner coupling/contact surfaces; and
    comprising a male instrument part which is inserted, relative to the female instrument part, at least partly through the hollow volume and therein can be pivoted about a pivot axis,
    the male instrument part defining in the coupling/hinge area a sliding guide portion having outwardly facing outer coupling/contact surfaces,
    wherein in the outer coupling/contact surfaces, a number of outer coupling recesses is arranged and on the inner coupling surfaces, a number of inner coupling recesses is arranged which extend relative to a longitudinal axis of the surgical instrument in a direction or directions other than that of the outer coupling recesses.

2. The surgical instrument according to claim 1, wherein the inner coupling recesses extend relative to the outer coupling recesses so that the female instrument part and the male instrument part are prepared for contacting each other in the coupling/hinge area at point and/or line contacts.

3. The surgical instrument according to claim 1, wherein the inner coupling recesses and/or the outer coupling recesses extend in trough shape and linearly over an entire width of the respective branch.

4. The surgical instrument according to claim 1, wherein the inner coupling recesses and/or the outer coupling recesses are in the form of a plurality of wave-shaped recesses.

5. The surgical instrument according to claim 1, wherein a profile of the inner coupling recesses and/or a profile of the outer coupling recesses forms a wave shape in a longitudinal section along the longitudinal axis.

6. The surgical instrument according to claim 1, wherein the direction of the inner coupling recesses is inclined relative to the longitudinal axis of the surgical instrument in a direction of rotation about the pivot axis at an angle $0° < \text{angle a} < 90°$ and the direction of the outer coupling recesses is inclined relative to the longitudinal axis in the opposite direction of rotation about the pivot axis at an angle $0° < \text{angle b} < -90°$.

7. The surgical instrument according to claim 1, wherein the female instrument part and the male instrument part along the pivot axis include such through-openings that in said through-openings a pivot pin can be arranged which produces a positive operative/pivot coupling between the female instrument part and the male instrument part.

8. The surgical instrument according to claim 7, wherein the male instrument part forms in an area around the through-opening thereof at least one chamfer.

9. The surgical instrument according to claim 7, wherein the through-opening of the male instrument part has a rectangular cross-section so that between the through-opening of the male instrument part and the pivot pin round in cross-section a line contact can be formed.

* * * * *